United States Patent
Smith

(10) Patent No.: US 9,539,137 B2
(45) Date of Patent: Jan. 10, 2017

(54) DISPOSABLE OSTOMY BAG

(75) Inventor: Rory Smith, Leatherhead (GB)

(73) Assignee: WELLAND MEDICAL LIMITED, Surrey (GB)

( * ) Notice: Subject to any disclaimer, the term of this patent is extended or adjusted under 35 U.S.C. 154(b) by 692 days.

(21) Appl. No.: 13/393,606

(22) PCT Filed: Apr. 26, 2010

(86) PCT No.: PCT/GB2010/000826
§ 371 (c)(1),
(2), (4) Date: Mar. 1, 2012

(87) PCT Pub. No.: WO2010/122314
PCT Pub. Date: Oct. 28, 2010

(65) Prior Publication Data
US 2012/0172823 A1 Jul. 5, 2012

(30) Foreign Application Priority Data
Sep. 2, 2009 (GB) .................................. 0915266.1

(51) Int. Cl.
*A61F 5/44* (2006.01)
*A61F 5/445* (2006.01)
(Continued)

(52) U.S. Cl.
CPC .............. *A61F 5/445* (2013.01); *A61F 5/441* (2013.01); *A61F 5/443* (2013.01); *A61F 2005/4402* (2013.01)

(58) Field of Classification Search
CPC .......... A61F 5/441; A61F 5/443; A61F 5/445; A61F 2005/4402
(Continued)

(56) References Cited

U.S. PATENT DOCUMENTS 5,330,454 A * 7/1994 Klingler et al. ............... 604/338
5,591,144 A * 1/1997 Smith et al. ................... 604/327
(Continued)

FOREIGN PATENT DOCUMENTS

GB 2290713 A 1/1996
GB 2434316 A 7/2007
(Continued)

OTHER PUBLICATIONS

International Search Report for PCT/GB2010/000826 mailed Jul. 14, 2010.
(Continued)

*Primary Examiner* — Tatyana Zalukaeva
*Assistant Examiner* — Andrew J Mensh
(74) *Attorney, Agent, or Firm* — Potter Anderson and Corroon LLP

(57) ABSTRACT

An ostomy bag (1) for receiving bodily waste comprising; an outer protective pouch (3) comprising a laminated material with an outer layer of water-impermeable material (15) and an inner layer of water-soluble material (13); an inner waste-collecting pouch (5) enclosed within the outer protective pouch (3) comprising a laminated material with an outer layer of water-soluble material (9) and an inner layer of water-impermeable material (7), and means (23) defining an orifice (19) to enable bodily waste to enter the inner pouch (5); wherein the outer protective pouch (3) is removeably sealed and both the outer protective pouch (3) and inner waste-collecting pouch (5) are of a structure which is weakened upon immersion in a toilet bowl to both become less buoyant such that the bag (1) can be flushed away.

30 Claims, 3 Drawing Sheets

(51) Int. Cl.
*A61F 5/441* (2006.01)
*A61F 5/443* (2006.01)

(58) Field of Classification Search
USPC .............................. 604/332, 333, 344, 345
See application file for complete search history.

(56) References Cited

U.S. PATENT DOCUMENTS

| | | | |
|---|---|---|---|
| 5,865,819 A * | 2/1999 | Cisko et al. | 604/339 |
| 2003/0036721 A1* | 2/2003 | Zhao et al. | 604/15 |
| 2005/0004539 A1* | 1/2005 | Brown et al. | 604/327 |
| 2005/0084634 A1* | 4/2005 | Giori | 428/35.2 |

FOREIGN PATENT DOCUMENTS

| | | |
|---|---|---|
| GB | 0907051.7 | 4/2009 |
| GB | 0915266.1 | 9/2009 |
| WO | WO 2005/041828 A2 | 5/2005 |

OTHER PUBLICATIONS

Textile Innovation and Knowledge Platform website, http://www.tikp.co.uk/knowledge/technology/coating-and-laminating (2016).

* cited by examiner

DISPOSABLE OSTOMY BAG

The present invention relates to ostomy bags and more specifically to ostomy bags which can be hygienically flushed down a toilet.

Ostomy bags for receiving bodily waste are well known. A major problem with existing bags is that it is difficult to dispose of a used bag in a convenient and hygienic manner. For example, some existing bags require a user to cut an edge of the bag to deposit the bag's content down a toilet, whilst the soiled bag is disposed of separately. The soiled bag needs to be wrapped and placed in a bin or incinerated. The disposal of a bag in this way is unhygienic, unpleasant and inconvenient for a user.

Various proposals have been made for ostomy bags which can be flushed down a toilet. However, there are significant disadvantages with the products that have been developed to date. The buoyancy, lack of degradability and bulk of used bags makes it difficult to flush them away. If the bags decompose readily to allow them to be flushed away, they are often not strong enough to be waterproof and withstand use. However, if the bags do not decompose readily they cause a pollution problem in the sewerage system and environmental damage following disposal.

The Applicant's earlier European patents EP0703762 and EP0768848 sought to overcome some of the problems described above by providing a removable inner bag provided within an outer bag. In use, the inner bag is sufficiently water-impermeable to prevent leakage but, when disposed of, would gradually dissolve to be flushed down a toilet after use. A material known to be suitable for this is a polymeric film formed from polyvinyl alcohol/polyvinyl acetate (PVOH). It is possible to obtain grades of PVOH which remain insoluble for a period of several days (i.e. the maximum time over which an ostomy bag would be worn) but have the advantage that they are water-softenable and over a more prolonged period they are biodegradable. The inner flushable bag is secured to the durable outer protective bag by a peelable connection. After use, when the inner bag is to be disposed of, the peelable connection is torn away and the inner bag has to be removed from the outer bag to be flushed down the toilet. The outer bag would not be soiled by the bodily waste but has to be disposed of separately, for example, with other household refuse. The removal of the inner bag still remains an inconvenience for a user and may be impractical for patients unable to carry out such tasks. Also the outer bag, which is not biodegradable, adds to landfill.

A peelable and flushable ostomy appliance is also disclosed in EP04795863. To allow disposal of the bag, a peelable sealing seam is broken such that the outer pouch walls are peeled away from the inner pouch. The inner pouch and its contents can be deposited in the bowl of a toilet and flushed away. However, the outer pouch walls need to be folded together and disposed of in some other manner, for instance in a pocket or a refuse container. The removal of the inner bag again is an inconvenience for a user and may be impractical for patients unable to carry out such tasks, such as the elderly or disabled. The outer bag, which is not biodegradable, adds to landfill.

The present invention sets out to provide an improved ostomy bag, which is convenient to use and overcomes the problems identified above by being suitable to be flushed down a toilet in its entirety.

In one aspect, the invention provides an ostomy bag for receiving bodily waste comprising;

an outer protective pouch comprising a laminate material with an outer layer of water-impermeable material and an inner layer of water-soluble material;

an inner waste-collecting pouch enclosed within the outer protective pouch comprising a laminate material with an outer layer of water-soluble material and an inner layer of water-impermeable material, and means defining an orifice to enable bodily waste to enter the inner pouch;

wherein the outer protective pouch is removeably sealed and both the outer protective pouch and the inner waste-collecting pouch are of a structure which is weakened upon immersion in a toilet bowl to become less buoyant such that the bag can be flushed away.

By removeably sealing the outer pouch, the outer pouch can be opened following use, without separating the inner and outer pouches. This allows water to contact the outer protective pouch's inner layer of water-soluble material and also contact the inner waste-collecting pouch's outer layer of water soluble material. When the bag is immersed in a toilet bowl, water enters the gap between the inner and outer pouches to break down the bag and allow it to be fully flushed away. A user is not required to remove the inner pouch from the outer pouch and can dispose of the entire bag.

It is to be understood that reference to the inner layer refers to the layer closest to the waste collected and the outer layer refers to the layer furthest from the waste collected.

Within the context of this specification the word "comprises" is taken to mean "includes, among other things". It is not intended to be construed as "consists of only".

Optionally, the inner and outer pouches are integrally formed as a multi-layered bag comprising:

an outer laminate sheet with an outermost layer of water-impermeable material and an inner layer of water-soluble material;

an inner laminate sheet with an outer layer of water-soluble material and an innermost layer of water-impermeable material.

An ostomy bag formed of a single sheet of laminate material improves the efficiency of manufacture of the bag. Preferably, the or each layer of the inner waste-collecting pouch is odour impermeable.

Preferably, the water-soluble material comprises polyvinyl acetate/polyvinyl alcohol.

Preferably, the water-soluble material is formed from biodegradable fibres.

Optionally, the water-soluble material is adapted to be hydrophobic.

An outermost layer of hydrophobic material allows a user to bathe or shower without the bag absorbing water and becoming uncomfortable to wear. A hydrophobic outer layer allows the bag to be dried and enhances the comfort of the bag when worn by a user.

Preferably, the water-impermeable material comprises ethylene vinyl alcohol, or silicon or TEFLON® (a synthetic fluoropolymer of tetrafluoroethylene (PTFE)), or a starch-based film, or a film that is physically modified such that its surface is hydrophobic.

Preferably, the water-impermeable material is plasma treated or coated with a hydrophobic layer.

It is envisaged that, by plasma treatment or coating, the water-impermeable material is adapted to be hydrophobic.

Preferably, the outer protective pouch comprises a peelable seal around at least part of its periphery.

Alternatively, the outer protective pouch comprises at least one aperture therein, wherein the aperture is removeably sealed by a peelable seal.

A peelable seal allows water to access the water soluble layers of the inner and outer bags without the need to totally separate the bags, which can prove difficult for some users, such as the elderly.

Preferably, the peelable seal comprises a pressure-sensitive adhesive.

More preferably, the peelable seal comprises at least one tab.

A tab assists in gripping of the seal to allow it to easily be peeled away from the outer pouch.

Optionally, the outer protective pouch further comprises an outermost layer of fibrous material.

An outermost layer of fibrous material is used as a comfort layer to make the bag more attractive to a user and more comfortable to wear next to the skin.

Preferably, the means defining the orifice further comprises a flange for securing the ostomy bag to the body wall of a patient, optionally an adhesive flange.

More preferably, the outer protective pouch and the inner waste-collecting pouch are connected together at the adhesive flange.

Still more preferably, the outer protective pouch and the inner waste-collecting pouch are connected together at the adhesive flange by a water-soluble bond or join.

Preferably, the outer water-soluble layer of the inner waste-collecting pouch further comprises a water-impermeable weld around its periphery.

The strength of the inner waste-collecting pouch is improved by including a water soluble weld line.

Preferably, the outermost wall of the outer protective pouch is provided with a flatus filter, optionally comprising activated charcoal.

A flatus filter permits gas to be exhausted from the bag, whilst filtering out malodorous gases.

Preferably, the activated charcoal is supported by a degradable polymer, such as polylactic acid.

More preferably, the filter is laminated on its major surfaces with a biodegradable film, such as polyvinyl acetate.

Preferably, the laminate material of the outer protective pouch has a thickness of between about 0.025 and 0.100 mm, wherein the outer layer of water-impermeable material has a thickness of between about 0.005 and 0.020 mm and the inner layer of water-soluble material has a thickness of between about 0.020 and 0.080 mm.

Preferably, the laminate material of the inner waste-collecting pouch has a thickness of between about 0.025 and 0.100 mm, wherein the outer layer of water-soluble material has a thickness of between about 0.005 and 0.020 mm and the inner layer of water-impermeable material has a thickness of between about 0.020 and 0.080 mm.

Within this specification, the term "about" is interpreted to mean optionally ±20%, preferably optionally ±10%, and more preferably optionally ±5%.

For the purposes of clarity and a concise description, features are described herein as part of the same or separate embodiments; however it will be appreciated that the scope of the invention, as defined by the claims, may include embodiments having combinations of all or some of the features described.

The invention will now be described by way of example with reference to the accompanying diagrammatic drawings, in which.

Figure 1:
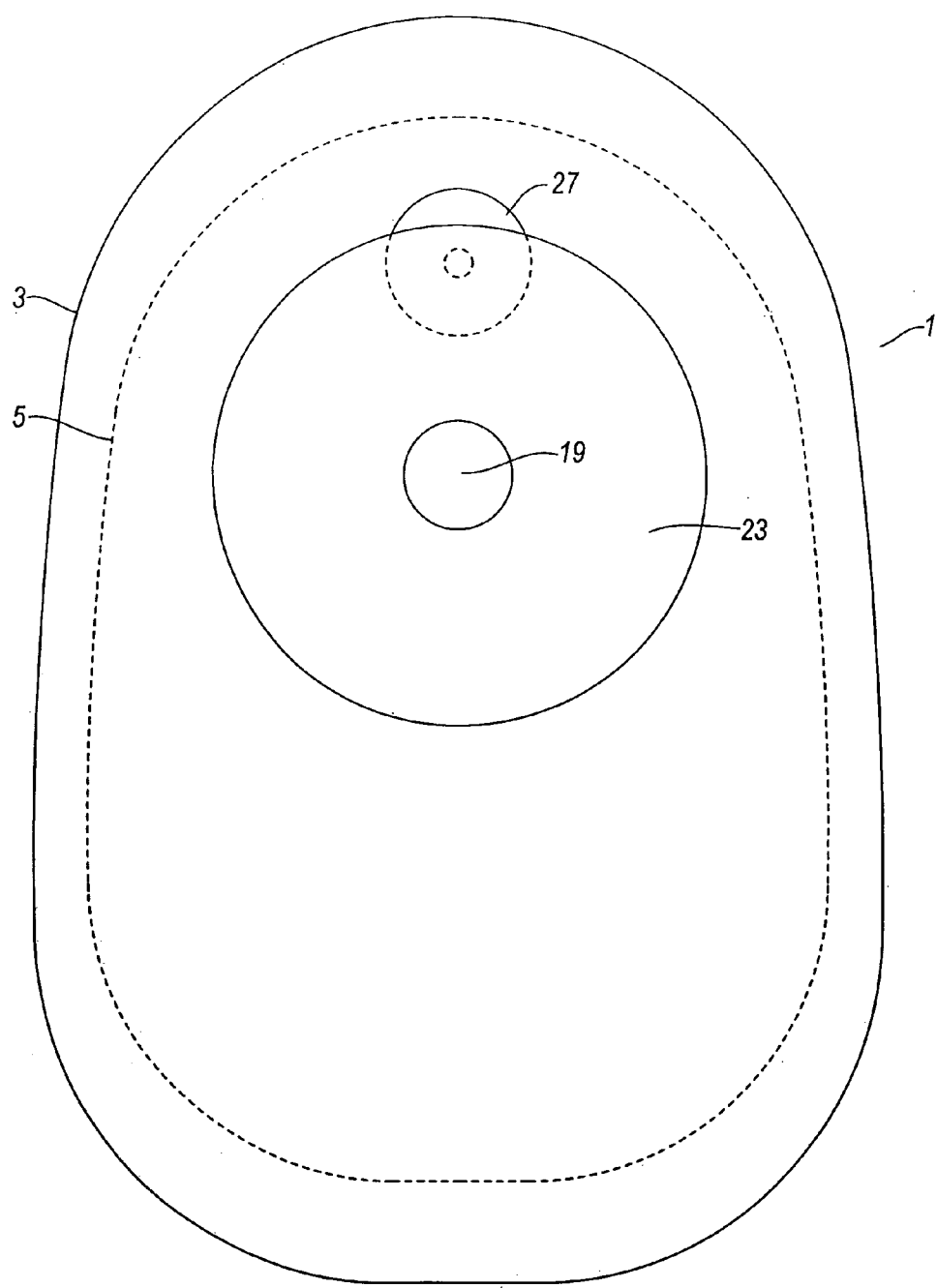
FIG. 1 is a view from one side of an ostomy bag constructed in accordance with the present invention.

Referring to the drawings, the ostomy bag 1 according to one embodiment of the invention comprises an outer protective pouch 3 and an inner waste-collecting pouch 5. The inner pouch 5 is made of a laminate material. The innermost layer 7 of the inner pouch 5 is a thin EVA (ethylene vinyl alcohol) film, such as DEV-07-04A from Exopack. The innermost layer 7 is waterproof and strong enough to contain bodily waste held therein and provides an odour barrier. The innermost EVA layer 7 is only a small proportion of the total thickness of the inner pouch 5, such that it is relatively insignificant to the bulk of the ostomy bag 1. This allows the bag 1 to be flushed away.

The innermost film 7 protects an outer soluble layer 9 of the inner waste-collecting pouch 5 from the contents of the bag. The outer layer 9 of the inner pouch 5 is a film formed from a water-soluble or water-disintegrable polymer, such as PVOH. Examples of suitable PVOH films are the Solubulun EF range available from Aichello Ltd, Japan.

The outer water soluble layer 9 of the inner pouch 5 comprises PVOH film which is soluble so that, when the inner waste-collecting pouch 5 is placed in water, the film dissolves or disintegrates. The PVOH film layer 9 is soluble above 60 degrees Celsius, but below 60 degrees Celsius the film absorbs water, stretches and slowly dissolves such that the inner pouch 5 is flushable. It has been found that PVOH film is also able to provide a good odour barrier, provided that the material is kept dry. Testing of suitable PVOH films and experimental data to support this assertion is described later.

Alternatively, the outer layer 9 of the inner waste-collecting pouch 5 is a TEFLON® or starch-based film such as Telratex I316 available from Donaldsons Limited or a silicone based film available from Specialty Silicone Fabricating.

The outer layer 9 of the inner pouch 5 is kept dry by the outer protective pouch 3. In one embodiment of the present invention the PVOH bonded material is also treated. For example, the outer surface 9 is plasma treated to modify its characteristics. This can provide further protection to the inner protective pouch 5

The laminate inner pouch 5 is sealed around its periphery either by heat sealing or an adhesive seam.

In a further embodiment of the present invention, a TEFLON®-based-film is used to make the inner pouch 5. The layers of the inner pouch 5 cannot be welded directly together to securely seal the inner pouch 5, because TEFLON® film has poor welding capabilities. EVA layers are used around the periphery of the inner pouch 5 to form a weld line 11, which extends around the periphery of the pouch 5. This EVA weld line 11 is printed onto the inner pouch 5, applied as thin strips or using a hot melt adhesive. The EVA weld line 11 does not dissolve when the bag 1 is flushed down the toilet, but is small enough not to interfere with flushing of the bag 1 following use.

The outer protective pouch 3 also comprises an EVA/PVOH laminate. The inner layer 13 of the outer protective pouch 3 comprises a PVOH fabric of film coated with an outer layer of EVA 15. At least part of the periphery of the outer protective pouch is held together by peelable seals 17. The seals 17 may also comprise tabs on their outer face to allow a user to grip the seals 17 with ease.

Figure 2:
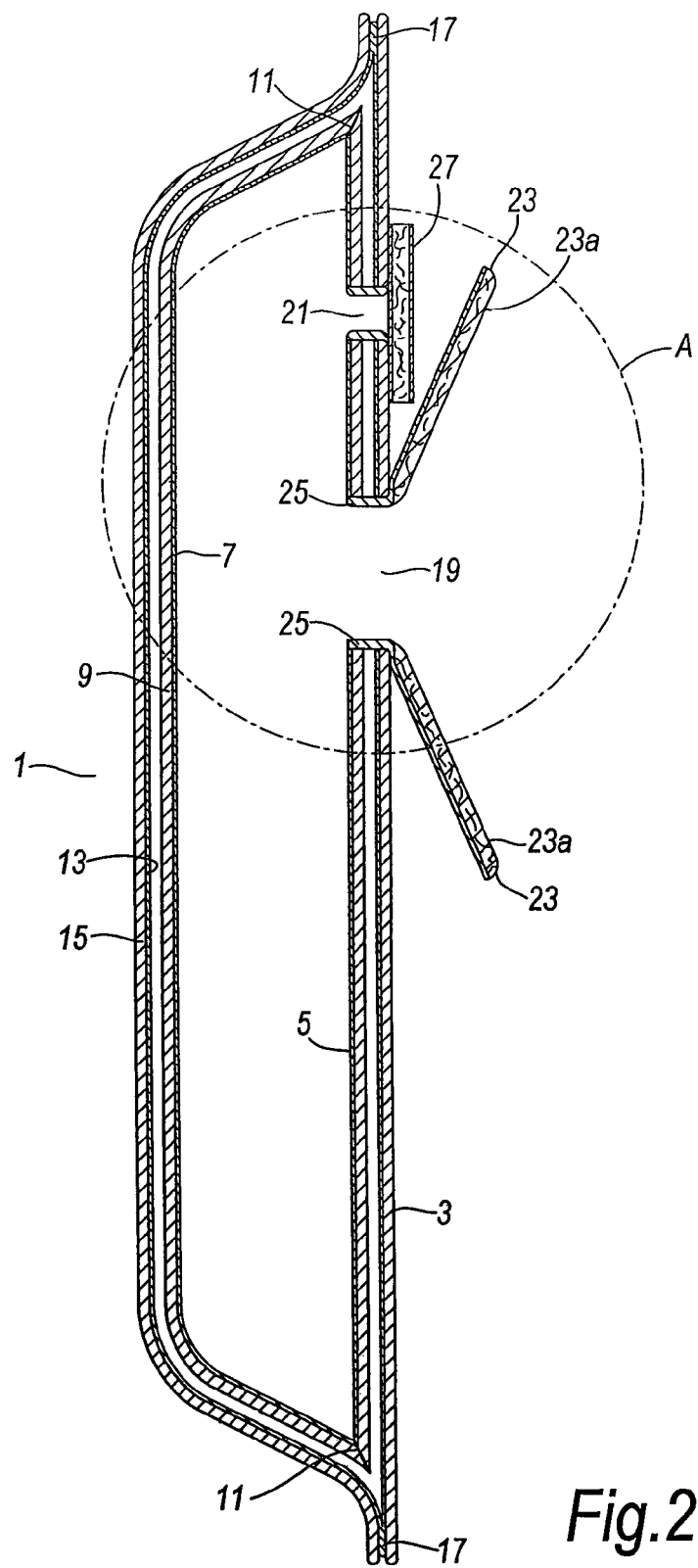
FIG. 2 is a sectional view of the ostomy bag of FIG. 1.

As shown in FIG. 2, the inner waste-collecting pouch 5 and the outer protective pouch 3 have openings 19, 21 in their body-side faces. Both pouches 3, 5 are welded together and to an annular flange 23 around the openings 19, 21. The adhesive flange may be of any known type. The welds 25 between the pouches 3, 5 and the annular flange 23 are formed of insoluble PVOH, which is biodegradable. The flange 23 is provided on its external surface with a layer of hydrocolloid adhesive 23a, which enables the bag 1 to be fixed to the body of a patient about the stomal opening. Prior to use, the adhesive 23a is covered by a release liner (not shown). The flange 23 and the hydrocolloid adhesive 23a are both soluble and/or biodegradable.

In a further embodiment of the present invention, an additional odour barrier layer (not shown) is laminated to the inner and outer pouches 3, 5. The odour barrier layer comprises a PVAlcohol, or PVacetate or an aluminosilicate based material. The odour barrier properties may be enhanced by the incorporation of nano-crystalline clays into the film structures. The use of an additional odour barrier layer is optional.

Figure 3:
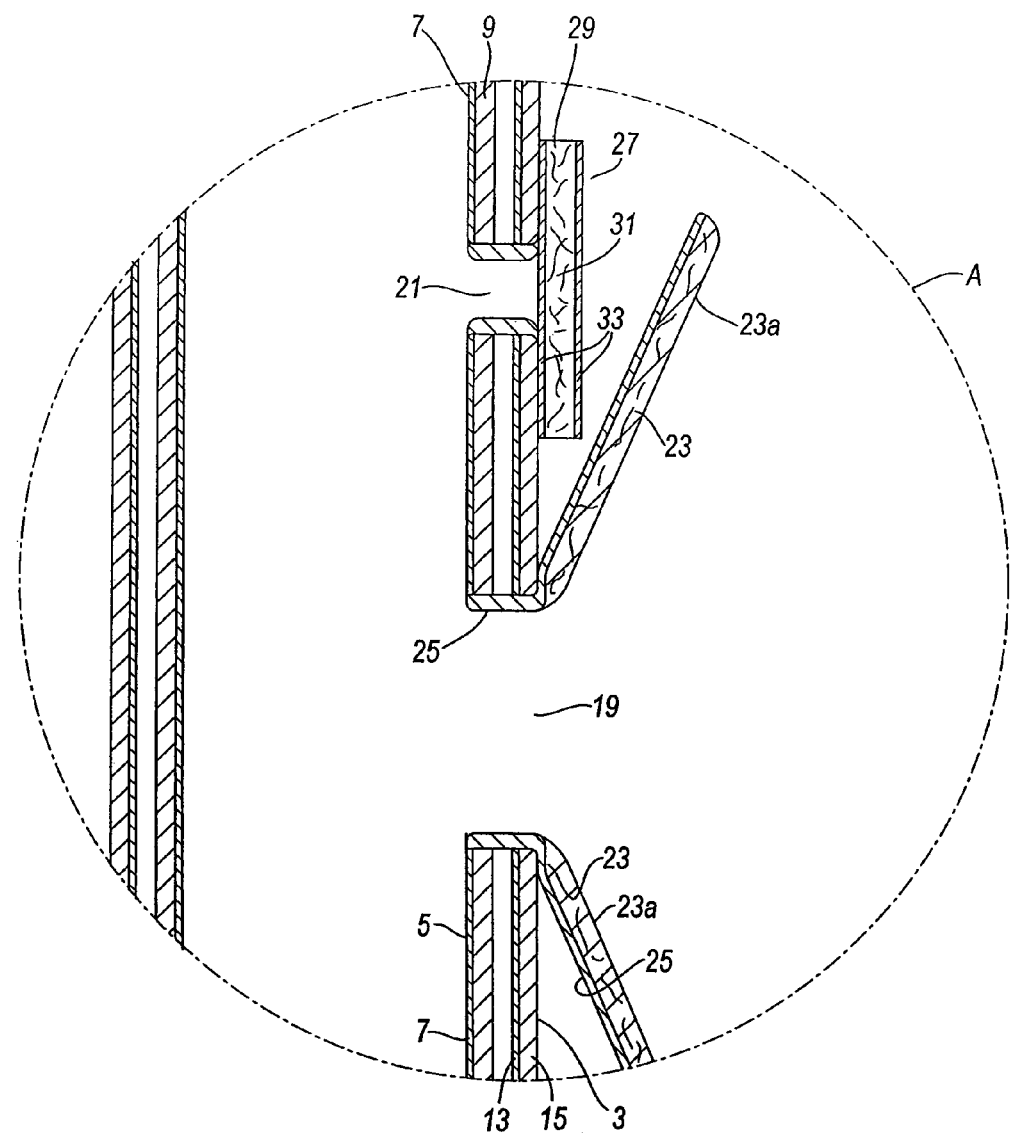
FIG. 3 is an enlarged view of the portion marked A in FIG. 2.

The bag 1 also comprises a flatus filter 27, which is shown in more detail in FIG. 3. The filter 27 comprises a layer of fabric 29 loaded with activated charcoal granules 31, sandwiched between two layers of PVOH 33. The fabric 29 holding the activated charcoal 31 comprises a polylactic acid film, or an insoluble PVOH fabric. In use, the filter 27 serves to allow flatus gases to escape from the bag 1, whilst malodorous components of the gases are retained within the filter 27 by the activated charcoal granules 33. The PVOH layers 33 sandwiching the activated charcoal are insoluble but biodegradable to allow the filter 27 to be flushed away with the bag 1, leaving only the activated carbon granules.

The assembly of the ostomy bag 1 of the present invention is formed by feeding the laminate material of the outer and inner pouches 3, 5 through cutting and sealing apparatus. Adhesive is applied around the periphery of the layers before the layers are heat sealed together to form the inner waste collecting pouch 5 and the outer protective pouch 3, shown in FIG. 2. In addition to the bag-forming apparatus, the present invention also makes use of laser cutting of the filter 27. The method and apparatus for laser-cutting the filter are described in the applicant's co-pending UK patent application no. 0803558.6.

In an alternative embodiment of the present invention, the inner and outer pouches are formed of a single sheet of laminate material. The innermost layers of the sheet are used to form the inner waste-collecting pouch 5 and the outermost layers form the outer protective pouch 3.

However, the bag 1 is cut and sealed from a single sheet of laminate material. The layers 3, 5 are separated by a gap, which, when the seal around the outer pouch 3 is removed, allows water to enter therebetween. The gap is shown in FIG. 2 as being continuous. In alternative embodiments of the present invention, the gap is discontinuous.

In use, a patient positions the ostomy bag 1 in the normal manner, attaching the annular flange 23 to the body wall. When the bag 1 is full, a user detaches the annular flange 23 and so the bag 1 from the body. The peelable seals 17 at the top and bottom of the outer protective pouch 3 are removed by gripping the tabs provided, whilst the inner pouch 5, containing the bodily waste, remains in tact. It is not necessary for a user to fully separate the inner and outer pouches 3, 5. The inner and outer pouches 3, 5 are still attached to each other by the PVOH welds at the openings 19, 21 of the bag 1. Alternatively, the inner bag is exposed to water by peeling off the flange 23 to allow water to enter between the inner and outer pouches 3, 5.

The bag 1 is then dropped into the bowl of a toilet. Water flows into the gap between the innermost layer 13 of the outer pouch 3 and the outermost layer 9 of the inner pouch 5. The water-soluble outer layer 9 of the inner bag 5 and the water-soluble inner layer 13 of the outer bag 3 rapidly dissolve and become limp, conforming more closely to the contours of the bag's contents and so reducing the buoyancy of the bag 1. The majority of the components of the annular flange 23 and the filter 27 also dissolve. The entire bag 1 can then be easily flushed away and the majority of the bag's component parts are biodegradable.

In a further embodiment of the present invention, means are also provided for accelerating the breakdown of the components of the bag 1. For example, a sachet of chemicals or enzymes is provided in the gap between the outer pouch 3 and the inner pouch 5 of the bag 1. A chemical or an enzyme reaction initiated when the sachet comes into contact with water in the toilet bowl accelerates the breakdown of the material of the bag 1. A chemical reaction leads to the modification of the polymer materials from which the bag 1 is made or side groups to that polymer. The enzyme's reaction specifically targets the polymer holding the structure of the bag 1 together. It is also envisaged that further triggers could accelerate the breakdown of the material of the bag 1 on immersion into the toilet water. For example, a change in pH or ionic strength could act as trigger. Heat via a exothermic or endothermic reaction can act as a trigger. A microbiological reaction could breakdown the bag 1 by use of a micro-organism which metabolises or uses the polymer holding the bag 1 together as a food source.

Other materials contemplated for use in the ostomy bag of the invention include (without limitation); a modified PVA laminate comprising a cold water soluble PVA or PVA related polymer as a core layer; an outer hydrophobic layer, for example; a polyvinyl butyrate, a polymer having undergone a surface treatment with, for example silane, silicone, TEFLON® or another water resistant coating. Alternatives to water degradable PVA polymers include PLAs and starch based polymers.

The laminate will include an odour barrier layer which might be combined with one of the other layers (the layer having dual functionality) or be a separate layer. Polymers may be treated to improve odour barrier properties, for example by coating with odour preventing materials, or incorporating materials into the polymer. In one particular example, the odour barrier layer is a polymer which has dispersed within it odour absorbing particles of a size which do not significantly impair the polymer's structural integrity. One example of a suitable particle material is clay particles, desirably the particles are nano-particles arranged to provide as large as possible surface area over which odour gases must pass to escape the pouch. The odour barrier layer may also be treated with cationic surfactants.

One specific, useful example of a base polymer which is both water soluble and is suited to modification as an odour barrier is marketed by Kuraray Specialities Europe GmbH as EXCEVAL.

The above described embodiments have been given by way of example only, and the skilled reader will naturally appreciate that many variations could be made thereto without departing from the scope of the claims.

Testing to Evaluate the Capabilities of PVOH Films as an Odour Barrier

Method

The following tests were conducted to determine the potential of a variety of films to act as an odour barrier for use as a film for an ostomy pouch. Composite polyvinyl alcohol (PVOH)/fluoropolymer films are of particular interest.

In order to evaluate the properties of PVOH films with a fluoropolymer odour barrier a modified version of the onion odour test, known as BS ISO 8670-3:2000, was conducted for the following samples:

1. samples of cast PVOH 75 micron with 3 micron fluoropolymer coating manufactured by Monosol AF Ltd;
2. samples of Monosol cast PVOH 75 micron with 3 micron fluoropolymer coating bonded at the edges. The sample is heat sealed so that the PVOH keys into the fluoropolymer surface;
3. samples of Monosol cast PVOH 75 micron with 3 micron fluoropolymer layer bonded at the edges (effectively a duplicate of sample 2);
4. polyethylene (PE) film;
5. barrier film made of standard EVA/PVDC/EVA laminate as discussed previously in the description of the present invention (a Welland Medical Ltd Ostomy film).
6. barrier film made of standard EVA/PVOH/EVA laminate as discussed previously in the description of the present invention (a Welland Medical Ltd Flushable Pouch Film).

All samples were conditioned at ambient conditions for not less than four hours before testing was conducted.

Test 1—No Moisture Present

In test 1, a sample of onion was placed in a sealed polyethylene (PE) bag at the bottom of a jig. The jig comprises a small machined metal pot with a lid configured to trap a circular disc of test material and a defined area open to the atmosphere to allow moisture vapour transpiration. Circular discs of the film sample were clamped in the jig above the onion with the fluoropolymer coating facing towards the onion. During testing, the PE bag contains any moisture, which escapes from the onion. The jigs were placed in a sealed container and placed in an oven at 38° C. for four hours. The container was then removed from the oven and olfactory tests were conducted to determine if an onion odour could be detected.

Test 2—Moisture from Onion Present

In test 2, a sample of onion was placed in the bottom of a jig, as described above, and circular discs of the film sample were clamped in the jig above the onion with the fluoropolymer coating facing towards the onion. The jigs were placed in a sealed container and placed in an oven at 38° C. for four hours. The container was then removed from the oven and olfactory tests were conducted to determine if an onion odour could be detected.

Test 3—Onion Moisture Vapour Against Fluoropolymer Side and Moisture Vapour Against PVOH Side.

In test 3, a sample of onion was placed in the bottom of a jig, as described above, and circular discs of the film sample were clamped in the jig above the onion with the fluoropolymer coating facing towards the onion. The jigs were placed in a sealed container containing water and placed in an oven at 38° C. for four hours. The container was then removed from the oven and olfactory tests were conducted to determine if an onion odour could be detected.

Test 4—Moisture Loss Test

In test 4 the film samples were placed in contact with a known amount of water and over a predetermined period of time, between 24 and 168 hours, the moisture loss was recorded.

Results

| Test 1 | | | | |
|---|---|---|---|---|
| | Presence of onion odour | | | |
| Sample | strong | slight | none | pass |
| 1 | | | ✓ | ✓ |
| 6 | | | ✓ | ✓ |

| Test 2 | | | | |
|---|---|---|---|---|
| | Presence of onion odour | | | |
| Sample | Strong | slight | none | pass |
| 1 | | | ✓ | ✓ |
| 2 | | | ✓ | ✓ |
| 3 | | ✓ | | |
| 5 | | | ✓ | ✓ |

N.B—there were possible sealing problems with sample 3, which could have resulted in the slight presence of onion odour. Samples 2 and 3 did not have the fluoropolymer coating laminated to the PVOH and when samples were punched out for testing it was found that the two films separated. This made it difficult for sealing in the jigs.

| Test 3 | | | | |
|---|---|---|---|---|
| | Presence of onion odour | | | |
| Sample | Strong | slight | none | pass |
| 1 | | ✓ | | |
| 2 | | ✓ | | |
| 3 | | ✓ | | |
| 4 | ✓ | | | |

| Test 4 | | | | | |
|---|---|---|---|---|---|
| Sample | Initial Weight (g) | +24 hrs | +96 hrs | +168 hrs | % moisture loss after 168 hrs |
| 1 | 315.82 | 315.82 | 315.80 | 315.77 | 0.25 |
| 2 | 327.86 | 327.86 | 327.86 | 327.86 | 0 |
| 3 | 329.52 | 329.52 | 329.51 | 329.51 | 0.05 |
| 5 | 325.63 | 325.63 | 325.63 | 325.62 | 0.05 |

Conclusions

A comparison of the results of Test 2 and Test 3 shows that the odour barrier properties of the PVOH films are adversely affected by moisture. All three samples failed Test 3, which highlights that the failure of odour barrier properties of the samples is likely to be because the PVOH film is adversely affected by moisture from the outside environment.

It was noted that the films could be improved if they were provided as a single structure capable of being welded to itself and other components of an ostomy bag, such as non-woven materials, filters, wafers etc.

Test 4 shows that fluoropolymer or other barrier layer coatings are an effective protective barrier to moisture with no loss of moisture after 24 hours and only 0.25% or less after 168 hours. It is concluded that a combination of fluoropolymer and PVOH can successfully maintain an odour barrier in the presence of moisture. It was observed that a PVOH film as an outside layer of a film is adversely affected by moisture. Thus, a double layer of PVOH film with protective coatings outermost is preferable.

The invention claimed is:

1. An ostomy bag for receiving bodily waste comprising;
   an outer protective pouch comprising a laminate material having an outer layer of water-impermeable material and an inner layer of water-soluble material;
   an inner waste-collecting pouch enclosed within the outer protective pouch comprising a laminate material having an outer layer of water-soluble material and an inner layer of water-impermeable material,
   and means defining an orifice to enable bodily waste to enter the inner pouch;
   wherein the outer protective pouch is removeably sealed and configured to be opened following use, without separating the inner and outer pouches to allow water to contact the outer protective pouch's inner layer of water-soluble material and also contact the inner waste-collecting pouch's outer layer of water soluble material so that upon immersion in a toilet bowl, water is capable of entering a gap between the inner and outer pouches to break down the bag and allow it to be fully flushed away without removing the inner pouch from the outer pouch;
   and both the outer protective pouch and the inner waste-collecting pouch are of a structure which is weakened upon immersion in a toilet bowl to become less buoyant such that the bag can be flushed away.

2. An ostomy bag according to claim 1 wherein the inner and outer pouches are integrally formed as a multi-layered bag comprising:
   an outer laminate sheet having an outermost layer of water-impermeable material and an inner layer of water-soluble material;
   an inner laminate sheet having an outer layer of water-soluble material and an innermost layer of water-impermeable material.

3. An ostomy bag according to claim 1, wherein at least one layer of the inner waste-collecting pouch is odour impermeable.

4. An ostomy bag according to claim 1, wherein the water-soluble material comprises polyvinyl acetate or polyvinyl alcohol.

5. An ostomy bag according to claim 1, wherein the water-soluble material is formed from biodegradable fibres.

6. An ostomy bag according to claim 1, wherein the water-soluble material is adapted to be hydrophobic.

7. An ostomy bag according to claim 1, wherein the water-impermeable material comprises ethylene vinyl alcohol.

8. An ostomy bag according to claim 1, wherein the water-impermeable material comprises silicon.

9. An ostomy bag according to claim 1, wherein the water-impermeable material comprises TEFLON® (a synthetic polymer of tetrafluoroethylene (PTFE)).

10. An ostomy bag according to claim 1, wherein the water-impermeable material comprises a starch-based film.

11. An ostomy bag according to claim 1, wherein the water-impermeable material comprises a film having a surface which is hydrophobic.

12. An ostomy bag according to claim 1, wherein the water-impermeable material is plasma treated or coated with a hydrophobic layer.

13. An ostomy bag according to claim 1, wherein the outer protective pouch comprises a peelable seal around at least part of its periphery.

14. An ostomy bag according to claim 1, wherein the outer protective pouch comprises at least one aperture therein and the aperture is removeably sealed by a peelable seal.

15. An ostomy bag according to claim 13 wherein the peelable seal comprises a pressure-sensitive adhesive.

16. An ostomy bag according to claim 13, wherein the peelable seal comprises at least one tab.

17. An ostomy bag according to claim 1, wherein the outer protective pouch further comprises an outermost layer of fibrous material.

18. An ostomy bag according to claim 1, wherein the means defining the orifice further comprises a flange for securing the ostomy bag to the body wall of a patient.

19. An ostomy bag according to claim 18 wherein the flange further comprises an adhesive.

20. An ostomy bag according to claim 18 wherein the outer protective pouch and the inner waste-collecting pouch are connected together at the flange.

21. An ostomy bag according to claim 20 wherein the outer protective pouch and the inner waste-collecting pouch are connected together at the flange by a water-soluble bond.

22. An ostomy bag according to claim 1, wherein the outer water-soluble layer of the inner waste-collecting pouch further comprises a water-impermeable weld around its periphery.

23. An ostomy bag according to claim 1, wherein the outermost wall of the outer protective pouch is provided with a flatus filter.

24. An ostomy bag according to claim 23 wherein the flatus filter comprises activated charcoal.

25. An ostomy bag according to claim 24 wherein the activated charcoal is supported by a degradable polymer.

26. An ostomy bag according to claim 25 wherein the degradable polymer is a polylactic acid.

27. An ostomy bag according to claim 23, wherein the filter is laminated on its major surfaces with a biodegradable film.

28. An ostomy bag according to claim 27 wherein the biodegradable film is a polyvinyl acetate.

29. An ostomy bag according to claim 1, wherein the laminate material of the outer protective pouch has a thickness of between 0.025 and 0.100 mm±20%, the outer layer of water-impermeable material has a thickness of between 0.005 and 0.020 mm±20% and the inner layer of water-soluble material has a thickness of between 0.020 and 0.080 mm±20%.

30. An ostomy bag according to claim 1, wherein the laminate material of the inner waste-collecting pouch has a thickness of between 0.025 and 0.100 mm±20%, wherein the outer layer of water-soluble material has a thickness of between 0.005 and 0.020 mm±20% and the inner layer of water-impermeable material has a thickness of between 0.020 and 0.080 mm±20%.

* * * * *